(12) United States Patent
Germain et al.

(10) Patent No.: US 10,537,227 B2
(45) Date of Patent: Jan. 21, 2020

(54) MEDICAL DEVICES AND METHODS

(71) Applicant: BOSTON SCIENTIFIC SCIMED, INC., Maple Grove, MN (US)

(72) Inventors: Aaron Germain, Campbell, CA (US); Michael D. Walker, San Francisco, CA (US); Jacob Roland, San Jose, CA (US); Jan Echeverry, San Jose, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 225 days.

(21) Appl. No.: 15/245,775

(22) Filed: Aug. 24, 2016

(65) Prior Publication Data

US 2017/0055811 A1    Mar. 2, 2017

Related U.S. Application Data

(60) Provisional application No. 62/210,617, filed on Aug. 27, 2015.

(51) Int. Cl.
*A61B 1/00* (2006.01)
*A61B 1/015* (2006.01)
*A61B 1/303* (2006.01)

(52) U.S. Cl.
CPC ...... *A61B 1/00135* (2013.01); *A61B 1/00128* (2013.01); *A61B 1/015* (2013.01); *A61B 1/303* (2013.01)

(58) Field of Classification Search
CPC ..... A61B 1/00135; A61B 1/015; A61B 1/303; A61B 1/00128; A61B 18/1206; A61B 18/1485
See application file for complete search history.

(56) References Cited

U.S. PATENT DOCUMENTS

| | | | |
|---|---|---|---|
| 4,116,198 A | 9/1978 | Roos | |
| 4,706,656 A | 11/1987 | Kuboto | |
| 4,994,026 A | 2/1991 | Fecondini | |
| 4,998,527 A | 3/1991 | Meyer | |
| 5,048,508 A | 9/1991 | Storz | |
| 5,152,746 A | 10/1992 | Atkinson et al. | |
| 5,176,629 A | 1/1993 | Kullas et al. | |
| 5,259,366 A * | 11/1993 | Reydel | A61B 1/00135 383/203 |
| 5,312,399 A | 5/1994 | Hakky et al. | |

(Continued)

FOREIGN PATENT DOCUMENTS

| | | |
|---|---|---|
| JP | 2007117289 A | 5/2007 |
| JP | 2008540041 A | 11/2008 |

(Continued)

*Primary Examiner* — Timothy J Neal
(74) *Attorney, Agent, or Firm* — Seager, Tufte & Wickhem, LLP

(57) ABSTRACT

A sheath adapter may be used within a medical device to provide one or more additional lumens. One sheath for use with a medical device may comprise a C-shaped elongate shaft extending from a proximal end to a distal end, the C-shaped elongate shaft configured to fit onto a shaft of the medical device and a lumen extending at least partially along a length of the elongate shaft, the lumen having a first port disposed proximate the distal end of the C-shaped elongate shaft and a second port disposed proximate the proximal end of the C-shaped elongate shaft.

14 Claims, 12 Drawing Sheets

(56) References Cited

U.S. PATENT DOCUMENTS

| | | | |
|---|---|---|---|
| 5,382,229 A | 1/1995 | Grabenkort et al. | |
| 5,392,765 A | 2/1995 | Muller | |
| 5,437,629 A | 8/1995 | Goldrath | |
| 5,456,689 A | 10/1995 | Kresch et al. | |
| 5,492,537 A | 2/1996 | Vancaillie | |
| 5,522,805 A | 6/1996 | Vancaillie et al. | |
| 5,556,378 A | 9/1996 | Storz et al. | |
| 5,807,240 A | 9/1998 | Muller et al. | |
| 5,814,009 A | 9/1998 | Wheatman | |
| 5,836,909 A | 11/1998 | Cosmescu | |
| 5,885,277 A | 3/1999 | Korth | |
| 5,921,953 A | 7/1999 | Novak et al. | |
| 5,941,815 A * | 8/1999 | Chang | A61B 1/00142 600/114 |
| 5,947,990 A | 9/1999 | Smith | |
| 6,032,673 A | 3/2000 | Savage et al. | |
| 6,039,748 A | 3/2000 | Savage et al. | |
| 6,113,594 A | 9/2000 | Savage | |
| 6,113,597 A | 9/2000 | Eggers et al. | |
| 6,159,160 A | 12/2000 | Hsei et al. | |
| 6,238,366 B1 | 5/2001 | Savage et al. | |
| 6,319,221 B1 | 5/2001 | Lee | |
| 6,979,332 B2 | 12/2005 | Adams | |
| 7,207,966 B2 | 4/2007 | Savare et al. | |
| 7,429,262 B2 | 9/2008 | Woloszko et al. | |
| 7,678,070 B2 | 3/2010 | Kumar et al. | |
| 7,918,822 B2 | 4/2011 | Kumar et al. | |
| 8,061,359 B2 | 11/2011 | Emanuel | |
| 8,062,214 B2 | 11/2011 | Shener et al. | |
| 8,226,549 B2 | 7/2012 | Kumar et al. | |
| 8,308,726 B2 | 11/2012 | Kumar et al. | |
| 8,388,570 B2 | 3/2013 | Kumar et al. | |
| 8,419,626 B2 | 4/2013 | Shener-Irmakoglu et al. | |
| 8,460,178 B2 | 6/2013 | Kumar et al. | |
| 8,512,283 B2 | 8/2013 | Kumar et al. | |
| 8,512,326 B2 | 8/2013 | Shadduck et al. | |
| 8,568,424 B2 | 10/2013 | Shugrue et al. | |
| 8,591,464 B2 | 11/2013 | Kumar et al. | |
| 8,597,228 B2 | 12/2013 | Pyles et al. | |
| 8,652,089 B2 | 2/2014 | Kumar et al. | |
| 8,728,066 B2 | 5/2014 | Shadduck et al. | |
| 8,840,625 B2 | 9/2014 | Adams et al. | |
| 8,840,626 B2 | 9/2014 | Adams et al. | |
| 8,852,085 B2 | 10/2014 | Shener-Irmakoglu et al. | |
| 8,911,363 B2 | 12/2014 | Kumar et al. | |
| 8,951,274 B2 | 2/2015 | Adams et al. | |
| 8,974,448 B2 | 3/2015 | Germain et al. | |
| 9,028,398 B2 | 5/2015 | Kumar et al. | |
| 9,060,760 B2 | 6/2015 | Sullivan et al. | |
| 9,072,431 B2 | 7/2015 | Adams et al. | |
| 9,084,847 B2 | 7/2015 | Klein et al. | |
| 9,095,366 B2 | 8/2015 | Sullivan et al. | |
| 9,155,453 B2 | 10/2015 | Kumar et al. | |
| 9,233,193 B2 | 1/2016 | Truckai et al. | |
| 9,254,142 B2 | 2/2016 | Germain et al. | |
| 9,439,677 B2 | 9/2016 | Germain et al. | |
| 9,439,720 B2 | 9/2016 | Germain et al. | |
| 9,486,233 B2 | 11/2016 | Bek et al. | |
| 9,498,244 B2 | 11/2016 | Orczy-Timko et al. | |
| 9,549,754 B2 | 1/2017 | Shadduck et al. | |
| 2002/0038122 A1 | 3/2002 | Peters | |
| 2005/0085695 A1 | 4/2005 | Benedict et al. | |
| 2005/0192532 A1 * | 9/2005 | Kucklick | A61M 25/0662 604/96.01 |
| 2007/0225559 A1 | 9/2007 | Clerc et al. | |
| 2008/0249366 A1 | 10/2008 | Gruber et al. | |
| 2009/0270895 A1 | 10/2009 | Churchill et al. | |
| 2009/0270896 A1 | 10/2009 | Sullivan et al. | |
| 2012/0078038 A1 | 3/2012 | Sahney et al. | |
| 2013/0046304 A1 | 2/2013 | Germain et al. | |
| 2013/0079702 A1 | 3/2013 | Klein et al. | |
| 2013/0103021 A1 | 4/2013 | Germain et al. | |
| 2013/0172805 A1 | 4/2013 | Germain et al. | |
| 2013/0172870 A1 | 7/2013 | Germain et al. | |
| 2013/0231652 A1 | 9/2013 | Germain et al. | |
| 2013/0296847 A1 | 11/2013 | Germain et al. | |
| 2014/0031834 A1 | 1/2014 | Germain et al. | |
| 2014/0114300 A1 * | 4/2014 | Orczy-Timko | A61B 17/32002 606/33 |
| 2014/0221997 A1 | 8/2014 | Shadduck et al. | |
| 2014/0236164 A1 | 8/2014 | Piskun | |
| 2014/0303551 A1 | 10/2014 | Germain et al. | |
| 2014/0324065 A1 | 10/2014 | Bek et al. | |
| 2015/0119795 A1 | 4/2015 | Germain et al. | |
| 2015/0157396 A1 | 6/2015 | Germain et al. | |
| 2015/0314048 A1 | 11/2015 | Klein et al. | |
| 2016/0089184 A1 | 3/2016 | Truckai et al. | |
| 2016/0106497 A1 | 4/2016 | Germain et al. | |
| 2016/0317219 A1 | 11/2016 | Germain et al. | |
| 2017/0014180 A1 | 1/2017 | Germain et al. | |

FOREIGN PATENT DOCUMENTS

| | | |
|---|---|---|
| JP | 2011120880 A | 6/2011 |
| JP | 2012532639 A | 12/2012 |
| JP | 2014512896 A | 5/2014 |

* cited by examiner

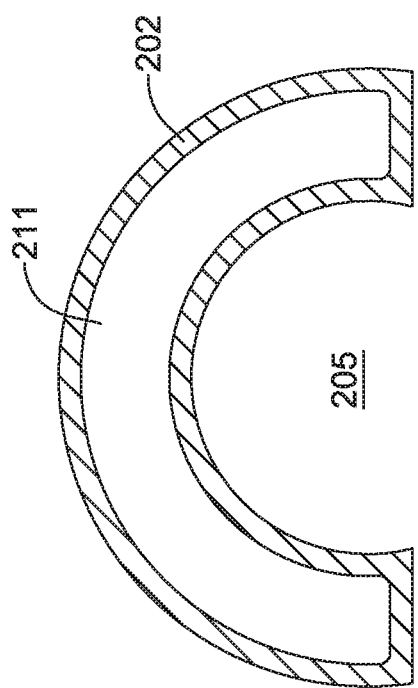

MEDICAL DEVICES AND METHODS

CROSS-REFERENCE TO RELATED APPLICATIONS

This application claims priority under 35 U.S.C. § 119 to U.S. Provisional Application Ser. No. 62/210,617, filed Aug. 27, 2015, the entirety of which is incorporated herein by reference.

TECHNICAL FIELD

The present disclosure relates to surgical devices and methods, for example for use in endoscopic and/or hysteroscopic procedures including resection and extraction of abnormal tissue such as fibroids and polyps.

BACKGROUND

Fibroids are non-cancerous tumors that develop in the wall of uterus. Uterine fibroids in particular occur in a large percentage of the female population, with some studies indicating up to 40 percent of all women have fibroids. Such fibroids can grow over time to be several centimeters in diameter and symptoms can include menorrhagia, reproductive dysfunction, pelvic pressure and pain.

One current treatment of fibroids is endoscopic or hysteroscopic resection or myomectomy. In relation to uterine fibroids, this involves transcervical access to the uterus with a hysteroscope together with insertion of a resecting instrument through a working channel in the hysteroscope. The resecting instrument may be an electrosurgical resection device such as a cutting loop. An electrosurgical resecting device is disclosed in U.S. Pat. No. 5,906,615. In other instances, a mechanical cutter may be used to remove the fibroid. Mechanical cutting devices are disclosed in U.S. Pat. Nos. 7,226,459; 6,032,673 and 5,730,752 and U.S. Published Patent Appl. 2009/0270898.

In a resection procedure, one step of the procedure includes distention of the operating cavity to create a working space for the procedure. In a relaxed state, body cavities tend to collapse with opposing walls in contact with one another. A fluid management system is used to distend the operating cavity to provide a working space. Fluid is administered through a passageway in the endoscope or hysteroscope or another device under sufficient pressure to expand or distend the body cavity. In some instances, the administered fluid may be taken up up by the body, such as through an exposed blood vessel, which may be termed intravasation. In general, this fluid uptake is undesirable and can even cause serious complications or even death.

SUMMARY

The present disclosure relates to surgical devices and methods, for example for use in endoscopic and/or hysteroscopic procedures including resection and extraction of abnormal tissue such as fibroids and polyps.

In one embodiment, a sheath for use with a medical device may comprise a C-shaped elongate shaft extending from a proximal end to a distal end, the C-shaped elongate shaft being configured to fit onto a shaft of the medical device. The sheath includes a lumen extending at least partially along a length of the elongate shaft, the lumen having a first port disposed proximate the distal end of the C-shaped elongate shaft and a second port disposed proximate the proximal end of the C-shaped elongate shaft.

Additionally, or alternatively, in any of the above embodiments, the lumen may be a first lumen, and the sheath may further comprise a second lumen having a first port disposed proximate the distal end of the C-shaped elongate shaft and a second port disposed proximate the proximal end of the C-shaped elongate shaft.

Additionally, or alternatively, in any of the above embodiments, the second port of the second lumen may be the second port of the first lumen.

Additionally, or alternatively, in any of the above embodiments, the first port of the lumen may be disposed on a distal-facing surface of the C-shaped elongate shaft.

Additionally, or alternatively, in any of the above embodiments, the first port of the lumen may be disposed on a side of the C-shaped elongate shaft.

Additionally, or alternatively, any of the above embodiments may further comprise a connecting member disposed at the second port of the lumen, wherein the connecting member is configured to connect to a pressure sensor.

Additionally, or alternatively, any of the above embodiments may further comprise a connecting member disposed at the second port of the lumen, wherein the connecting member is configured to connect to a fluid line.

Additionally, or alternatively, any of the above embodiments may further comprise a connecting member disposed at the second port of the lumen, wherein the connecting member is configured to connect to an aspiration line.

Additionally, or alternatively, in any of the above embodiments, the C-shaped elongate shaft may be configured to securely snap onto the shaft of the medical device.

Additionally, or alternatively, in any of the above embodiments, the C-shaped elongate shaft may have a circularly shaped cross-section with a gap having a gap width, the cross-section defining a channel having a channel diameter, and wherein the gap width is less than the channel diameter.

Additionally, or alternatively, in any of the above embodiments, the C-shaped elongate shaft may be configured to flex in order to fit onto the shaft of the medical device.

Additionally, or alternatively, in any of the above embodiments, the medical device may comprise an endoscope.

In another embodiment, a medical device system includes a hysteroscope and a sheath adapter. The hysteroscope includes a longitudinally extending shaft having a shaft diameter, and one or more lumens extending along at least a portion of the shaft. The sheath adapter includes an elongate shaft extending from a proximal end to a distal end, with a wall of the elongate shaft defining a channel having a longitudinally extending opening. A lumen extends at least partially along a length of the elongate shaft and within the wall of the shaft. The lumen has a first port disposed proximate the distal end of the elongate shaft and a second port disposed proximate the proximal end of the elongate shaft. The hysteroscope shaft is configured to fit within the channel.

Additionally, or alternatively, in any of the above embodiments, the lumen is a first lumen, and the sheath further comprises a second lumen having a first port disposed proximate the distal end of the elongate shaft and a second port disposed proximate the proximal end of the elongate shaft, wherein the second port of the second lumen is the second port of the first lumen.

Additionally, or alternatively, in any of the above embodiments, a width of the longitudinally extending opening of the channel is smaller than the shaft diameter of the hysteroscope, and the wall of the elongate shaft is configured to flex to receive the hysteroscope through the longitudinally extending opening of the channel within the channel.

In another embodiment, a medical device sheath may comprise an elongate shaft extending from a proximal end to a distal end. The elongate shaft has a channel extending from the proximal end to the distal end, wherein a wall of the elongate shaft only partially surrounds the channel. The channel is configured to receive a shaft of a medical device therein. The sheath includes a lumen extending at least partially along a length of the elongate shaft within the wall of the elongate shaft, the lumen having a proximal port disposed proximate the proximal end of the elongate shaft and a distal port disposed proximate the distal end of the elongate shaft.

Additionally, or alternately, in any of the above embodiments, a connection member may be disposed at the proximal end of the elongate shaft, the connection member being configured to connect to a medical device.

Additionally, or alternatively, in any of the above embodiments, the connection member may comprise a J-shaped slot.

Additionally, or alternatively, in any of the above embodiments, the medical device may be an endoscope or a hysteroscope.

Additionally, or alternatively, in any of the above embodiments, the channel may have a channel diameter, and wherein the channel diameter is less than or equal to a diameter of the shaft of the medical device.

Additionally, or alternatively, in any of the above embodiments, the channel may have an opening extending in a longitudinal manner along at least a portion of the elongate shaft, wherein a width of the opening is smaller than a diameter of the shaft of the medical device, and wherein the wall of the elongate shaft is configured to flex to receive the shaft of the medical device through the longitudinally extending opening of the channel within the channel.

In yet another embodiment, a medical device system may comprise a hysteroscope comprising: a longitudinally extending shaft, and one or more lumens extending along at least a portion of the shaft. The system may further include a sheath adapter comprising an elongate shaft extending from a proximal end to a distal end, a wall of the elongate shaft defining a channel having a longitudinally extending lateral opening, and a lumen extending at least partially along a length of the elongate shaft and within the wall of the shaft, the lumen having a first port disposed proximate the distal end of the elongate shaft and a second port disposed proximate the proximal end of the elongate shaft, wherein the hysteroscope shaft is configured to fit within the channel.

Additionally, or alternatively, in any of the above embodiments, the shaft of the hysteroscope has an outer diameter and the channel of the sheath has an inner diameter, wherein the inner diameter of the channel is less than or equal to the outer diameter of the shaft of the hysteroscope.

Additionally, or alternatively, in any of the above embodiments, a width of the longitudinally extending lateral opening of the channel may have smaller than the shaft diameter of the hysteroscope, and wherein the wall of the elongate shaft is configured to flex to receive the hysteroscope through the longitudinally extending lateral opening of the channel within the channel.

The above summary of some embodiments is not intended to describe each disclosed embodiment or every implementation of the present disclosure. The Figures, and Detailed Description, which follow, more particularly exemplify these embodiments.

BRIEF DESCRIPTION OF DRAWINGS

The disclosure may be more completely understood in consideration of the following detailed description of various embodiments of the disclosure in connection with the accompanying drawings, in which:

FIG. 4 is an example cross-sectional view of the exemplary sheath adapter of FIGS. 3A-3B as viewed along line A-A of FIG. 3A;

Figure 1:
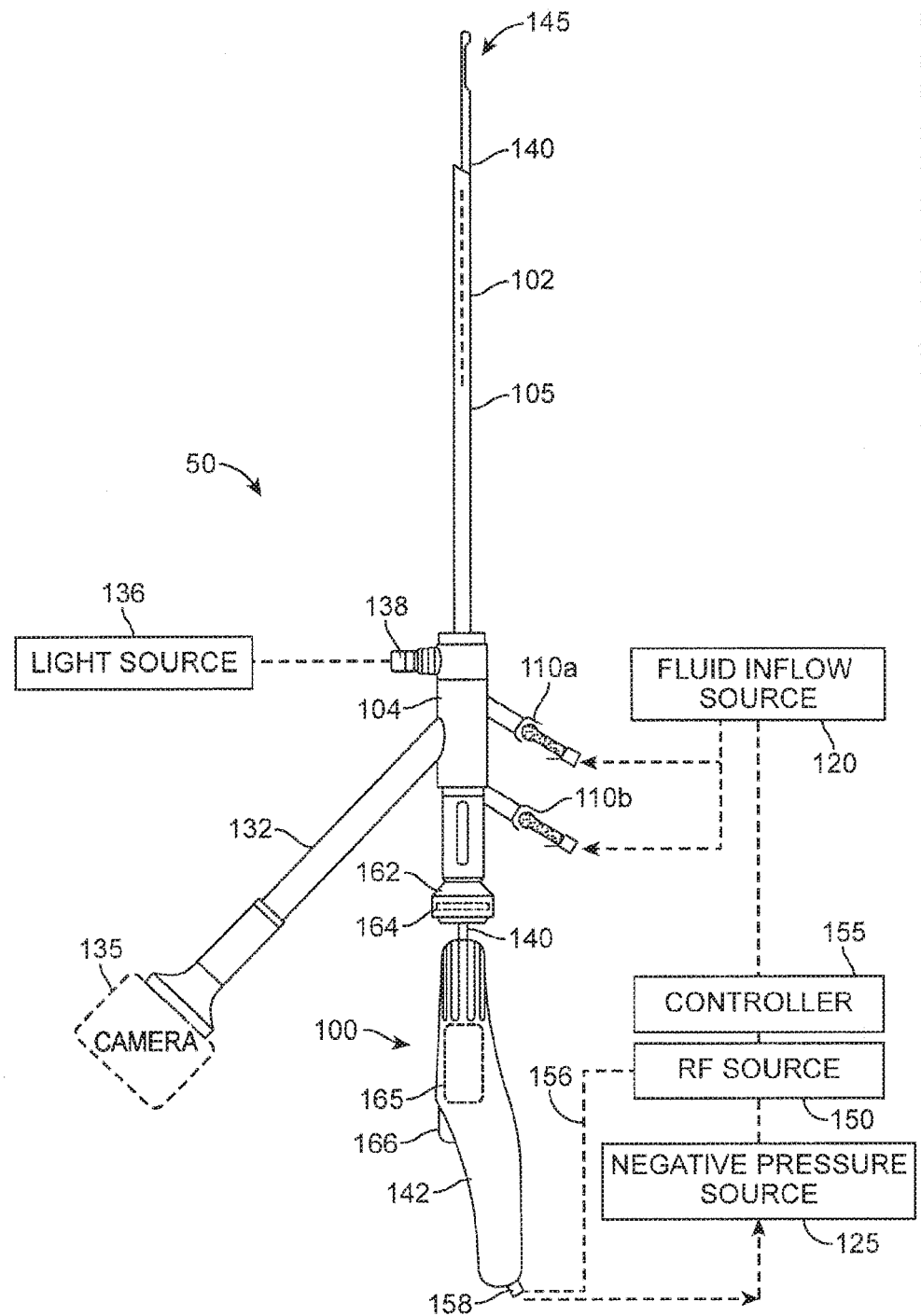
FIG. 1 is a plan view of an assembly including a hysteroscope and a tissue-resecting device inserted through the working channel of the hysteroscope.

While the disclosure is amenable to various modifications and alternative forms, specifics thereof have been shown by way of example in the drawings and will be described in detail. It should be understood, however, that the intention is not to be limited to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

Figure 2:
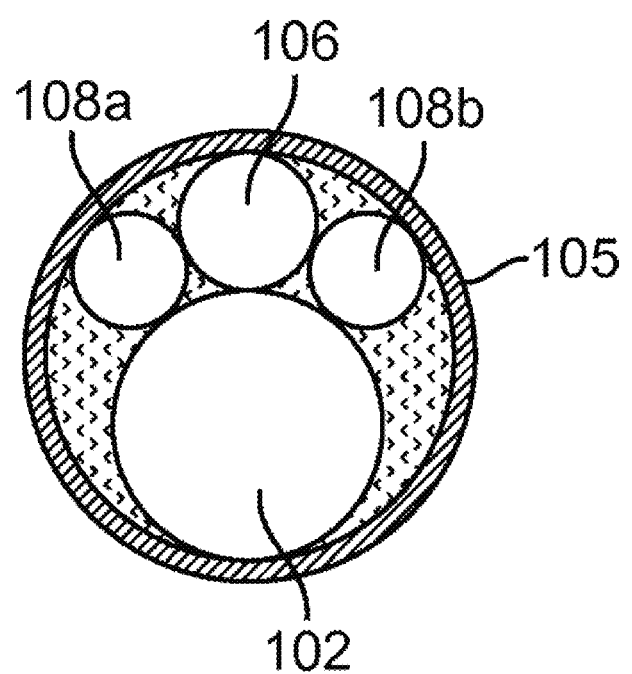
FIG. 2 is a cross-sectional view of the shaft of the hysteroscope of FIG. 1 showing various channels extending through at least a portion of the hysteroscope.

FIG. 1 illustrates an assembly that comprises endoscope or hysteroscope 50 that may be used for hysteroscopy or other similar procedures together with tissue resecting device 100 extending through a working channel 102 of endoscope 50. Endoscope 50 has handle 104 coupled to elongated shaft 105 and may have an outer diameter of between about 2 mm to about 9 mm. For instance, endoscope 50 used for diagnostic purposes may have an outer diameter of about 2 mm to about 5 mm or about 2 mm to about 4 mm, for example. Endoscope 50 used for operative procedures may have an outer diameter of about 5 mm to about 9 mm, about 6 mm to about 9 mm, or about 5 mm to about 7 mm, for example. Working channel 102 of endoscope 50 may extend through endoscope 50 and may be round, D-shaped or any other suitable shape. Elongated shaft 105 of endoscope 50 may further be configured with optics channel 106 and one or more fluid inflow/outflow channels 108a, 108b (FIG. 2). The one or more fluid inflow/outflow channels 108a, 108b may communicate with valve-connectors 110a, 110b configured for coupling to fluid inflow source 120, or optionally negative pressure source 125.

Fluid inflow source 120 may comprise a fluid container or reservoir 128 and fluid contained within fluid reservoir 128. The fluid inflow source 120 may be connected to a fluid management system which may control the flow of fluid through fluid inflow/outflow channels 108a, 108b and into/out of the operating cavity. For example, the fluid management system may include one or more pumps and possibly a pressure sensor for determining a pressure inside the operating cavity. In some embodiments, the fluid management system may be configured to regulate the fluid flow through fluid inflow/outflow channels 108a, 108b in order to maintain a desired pressure within the operating cavity. Exemplary closed system fluid management systems are described in US 2013/0172805, US 2013/0079702, US 2014/0303551 and US 2015/0119795, each of which is herein incorporated by reference in its entirety.

Handle 104 of endoscope 50 can include angled extension portion 132 with optics to which videoscopic camera 135 can be operatively coupled. Light source 136 may further be coupled to light coupling 138 on handle 104 of endoscope 50.

Working channel 102 of endoscope 50 is generally configured for insertion and manipulation of tissue-resecting device 100, for example to treat and remove fibroid tissue. In one embodiment, elongated shaft 105 has an axial length of 21 cm, and can comprise a 0° scope, or 15° to 30° scope. However, in other embodiments, the dimensions of elongated shaft 105 may differ.

Still referring to FIG. 1, tissue-resecting device 100 may have a highly elongated shaft assembly 140 configured to extend through working channel 102 in endoscope 50. Handle 142 of tissue-resecting device 100 may be adapted for manipulating the electrosurgical working end 145 of the device. In use, handle 142 can be manipulated both rotationally and axially, for example, to orient working end 145 to resect targeted fibroid tissue.

Where tissue-resecting device 100 is an electrosurgical device, tissue-resecting device 100 may have subsystems coupled to its handle 142 to enable electrosurgical resecting of targeted tissue. In these embodiments, a radiofrequency generator or RF source 150 and controller 155 may be coupled to at least one RF electrode carried by the working end. In one embodiment shown in FIG. 1, an electrical cable 156 and negative pressure source 125 are operatively coupled to connector 158 in handle 142. Electrical cable 156 couples RF source 150 to the electrosurgical working end 145. Negative pressure source 125 may communicate with a tissue extraction channel in shaft assembly 140 of tissue extraction device 100.

FIG. 1 further illustrates seal housing 162 that hysteroscope 50 may include which carries flexible seal 164 carried by endoscope handle 104 for sealing shaft 140 of tissue-resecting device 100 in working channel 102 to prevent distending fluid from escaping from the operating cavity.

In at least one embodiment as shown in FIG. 1, handle 142 of tissue-resecting device 100 may include motor drive 165 for reciprocating or otherwise moving a resecting component of the electrosurgical working end 145. Handle 142 may optionally include one or more actuator buttons 166 for actuating the device. In another embodiment, a footswitch can be used to operate the device. In various embodiments, the system includes a switch or control mechanism to provide a plurality of reciprocation speeds, for example 1 Hz, 2 Hz, 3 Hz, 4 Hz and up to 8 Hz. Further, the system can include a mechanism for moving and locking the reciprocating resecting sleeve in a non-extended position and in an extended position. Additionally, or alternatively, the system can include a mechanism for actuating a single reciprocating stroke.

As mentioned, in some embodiments, a pressure sensor may be connected to one or more of channels 106, 108a, or 108b of endoscope 50 in order to monitor intra-cavity pressure. In such embodiments, the pressure sensor may be connected to fittings 110a, 110b, or 138 and seal off the corresponding channel. When endoscope 50 is inserted into the body cavity and distension fluid is pumped into the body cavity, the distension fluid may traverse up the sealed channel to contact the pressure sensor, forming a static column of fluid within the channel communicating with the pressure sensor. This turns the channel into a static pressure channel, through which intra-cavity pressure is transferred to the pressure sensor. In this manner, the pressure sensor may monitor the intra-cavity pressure without being physically placed within the body cavity. However, in some procedures, all of channels 106, 108a, or 108b may be utilized for other purposes, such as fluid inflow/outflow, optics, and tissue evaluation and resection devices. Accordingly, in these cases, none of the existing channels may be available for use as a static pressure channel. Alternatively, it may be advantageous to add an additional channel to the system for fluid inflow/outflow, pressure monitoring, or another function.

Figure 3A:
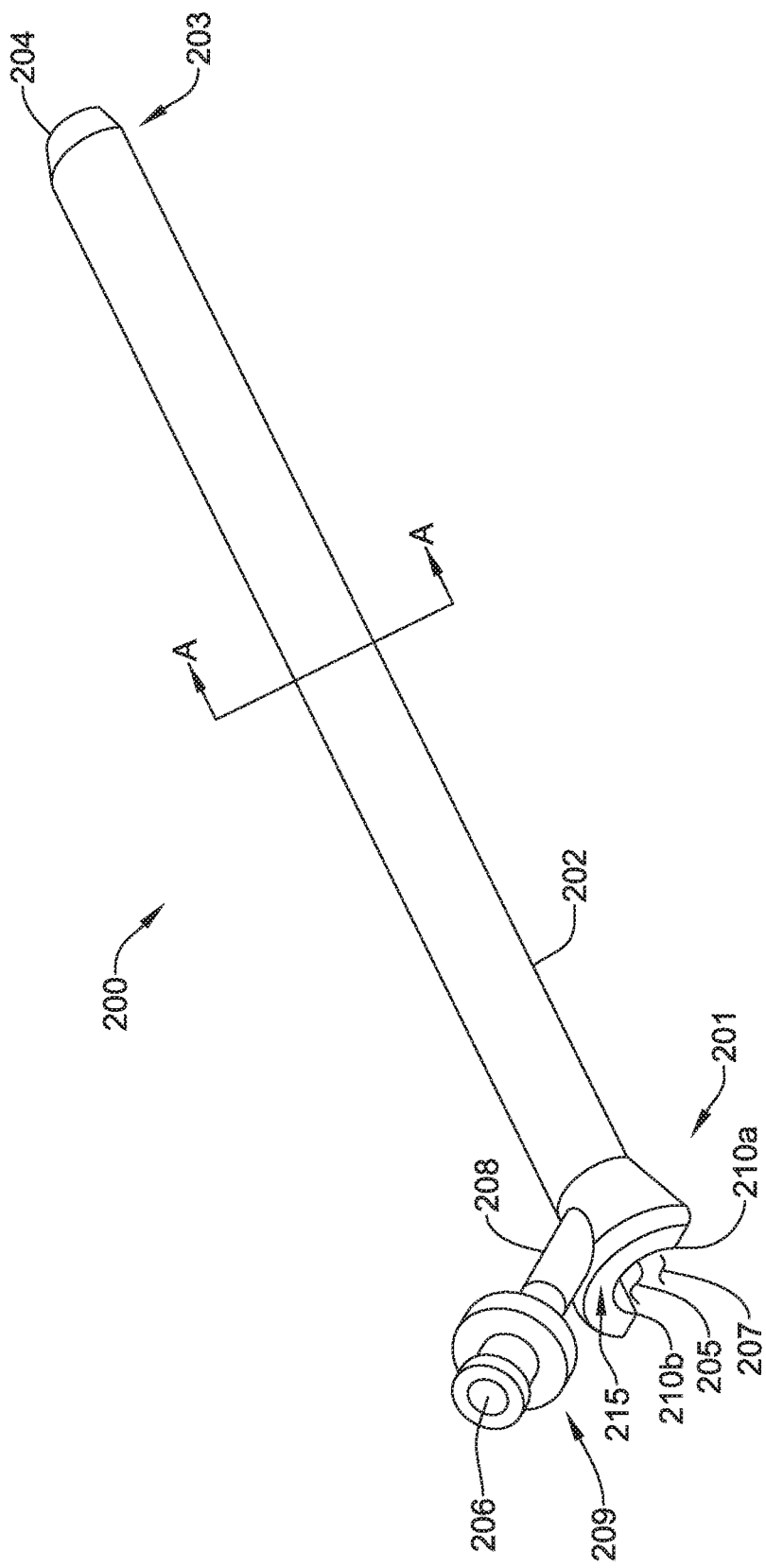
FIG. 3A is a perspective view of an exemplary sheath adapter that may be used in conjunction with the hysteroscope of FIG. 1.

FIG. 3A is a perspective view of exemplary attachment, termed sheath adapter 200 herein, for an endoscope, such as a hysteroscope, or the like, to provide one or more additional channels, for use as static pressure channel, a fluid inflow channel, a fluid outflow channel, and/or other uses. Sheath adapter 200 comprises elongate shaft 202 extending from proximal end 201 to distal end 203. Elongate shaft 202 may be generally C-shaped and may define a channel 205 running a length of elongate shaft 202 between the proximal end 201 and the distal end 203. In some embodiments, elongate shaft 202 may additionally define one or more lumens formed in the wall of elongate shaft 202 that extend proximate distal end 203 to proximate proximal end 201. In some embodiments, a lumen may have a distal port disposed on distal face 204, and the lumen may extend along elongate shaft 202 to port 206 disposed proximate proximal end 201. However, in other embodiments, the lumen may have a distal port disposed on the side of elongate shaft 202, such as proximate distal end 203. In at least some embodiments, port 206 may be situated on extension 208. Where elongate shaft 202 includes multiple lumens, the lumens may have different ports disposed proximate distal end 203, but may all converge and have the same port 206 proximate proximal end 201.

Extension 208 may extend generally away from elongate shaft 202. In some embodiments, extension 208 may include connecting portion 209 disposed at port 206. Connecting portion 209 may be a luer-fitting for sealingly attaching lines or devices, such as fluid inflow/outflow lines, aspiration lines, a pressure sensor, or other devices. For instance, when a line or device is attached to connecting portion 209, connecting portion 209 may form a fluid-tight seal with a fluid line or medical device so that any liquid that traverses port 206 does not escape. In other embodiments, connecting portion 209 may comprise other fittings for attaching lines or devices, some of which may comprise sealing connections, while others may not necessarily sealingly attach lines or devices.

Channel 205 may be designed to accommodate a variety of different shaft sizes, for example shafts having sizes between about 21 French to about 29 French, which correspond to outer diameters of about 6.5 mm to about 9.0 mm. These shaft sizes may correspond to various available endoscope or hysteroscope sizes. However, gap 207, defined between edges 210a, 210b of elongate shaft 202, may have a width that is less than the diameter of channel 205. Edges 210a, 210b may extend the entire length of sheath adaptor 200, allowing lateral access into the channel 205. Accordingly, sheath adapter 200 may be connected to such endoscope or hysteroscope shafts by snapping or sliding onto such shafts to securely connect sheath adapter 200 the endoscope or hysteroscope shafts. Once connected, as gap 207 is smaller than the diameter of the connected endoscope or hysteroscope shaft, the endoscope or hysteroscope shaft may not be easily disconnected or pulled out of channel 205.

In at least some embodiments, proximal end 201 of sheath adapter 200 may be configured to connect to an endoscope or hysteroscope. For instance, proximal end 201 may further include J-connection 215 disposed proximate proximal end 201. J-connection 215 may be a slot configured to engage with one or more corresponding projections or pins on an endoscope or hysteroscope to create a non-slidable connection between the endoscope or hysteroscope and sheath adapter 200.

In this manner, sheath adapter 200 may be used with a variety of different endoscopes or hysteroscopes. In some embodiments, sheath adapter 200 may provide an extra lumen for an endoscope or hysteroscope to allow for use with a fluid management system. For example, in instances where all of the channels of the endoscope or hysteroscope are in use, including at least one channel used for fluid inflow and one channel used for fluid outflow, a pressure sensor may be attached to connecting portion 209. This would turn the lumen or lumens connected to port 206 into static pressure channel, allowing the pressure sensor to monitor the intra-cavity pressure. In other embodiments, the pressure sensor may be attached to one of the channels of the endoscope or hysteroscope, and the lumen or lumens connected to port 206 may be used as a fluid inflow or outflow channel. For instance, a line may be connected to connecting portion 209 that is attached to a pump that is configured to pump fluid into the body cavity (inflow channel) or the line may be connected to a fluid reservoir to receive fluid from the body cavity or a pump to pump fluid out of the body cavity (outflow channel). In still other embodiments, a different device, such as a camera or light source, may be connected to connecting portion 209 and may extend through the lumen or lumens connected to port 206, allowing the channels of the endoscope or hysteroscope to be used for other purposes.

Figure 3B:
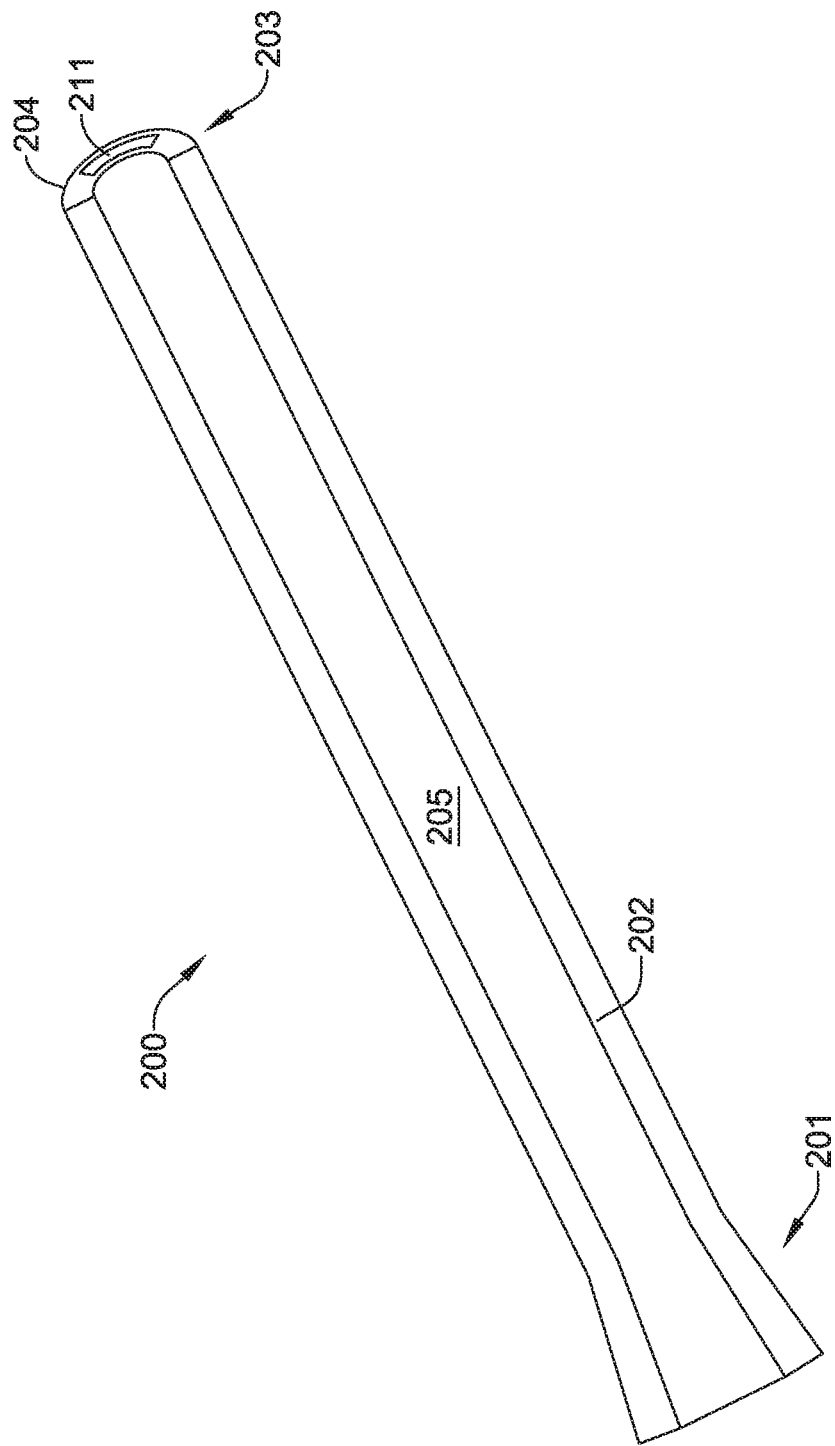
FIG. 3B is another perspective view of an exemplary sheath adapter that may be used in conjunction with the hysteroscope of FIG. 1.

FIG. 3B depicts sheath adapter 200 shown from a bottom view. As can be seen channel 205 may extend the entire length of elongate shaft 202. Additionally, lumen 211 can be seen opening on distal face 204 of elongate shaft 202. Further shown in FIG. 3B is the gap 207 having a width measured between edges 210a, 210b. The gap 207 permits lateral insertion of a shaft of an endoscope, such as a hysteroscope into channel 205 as the shaft passes between edges 210a, 210b. Gap 207, and thus edges 210a, 210b, may extend the entire length of sheath adaptor 200.

FIG. 4 depicts an example cross-section of sheath adapter 200 taken along line A-A in FIG. 3A. As can be seen in FIGS. 3A, 3B, and 4, sheath adapter 200 may include a single lumen 211. Lumen 211 may extend the length of sheath adapter 200 from distal face 204 to proximal end 201, and connecting to port 206. In some embodiments, elongate shaft 202 can be an extruded shaft, with lumen 211 formed in the wall of elongate shaft 202 during the extrusion process. Additionally, although lumen 211 is depicted as generally conforming to the shape of elongate shaft 202, it should be understood that lumen 211 may take any desired shape. For example, lumen 211 may have a circular, oval, square, oblong or any other shape. In still other embodiments, lumen 211 may be configured to receive a specific device and, so, may be shaped to complement the shape of the specific device.

Figure 5:
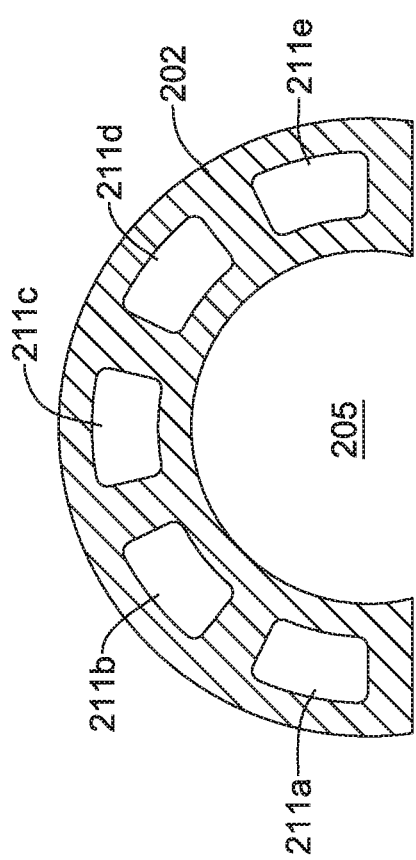
FIG. 5 is another example cross-sectional view of the exemplary sheath adapter of FIGS. 3A-3B as viewed along line A-A of FIG. 3A.

In other embodiments, sheath adapter 200 may include a plurality of lumens. For instance, FIG. 5 depicts another example cross-section of sheath adapter 200 taken along line A-A in FIG. 3A, where sheath adapter 200 includes multiple lumens 211a-211e. In these embodiments, each of lumens 211a-211e may extend along the length of elongate shaft 202 and merge with port 206 at proximal end 201. Also, each of lumens 211a-211e may have a separate port disposed on distal face 204 or may converge to a single port disposed on distal face 204 or disposed on a sidewall of the shaft 202 proximate distal end 201. In some instances, each of the plurality of lumens 211a-211e may extend distally to a separate port disposed on a sidewall of shaft 202 proximate distal end 201. Each distal port may be arranged circumferentially and/or longitudinally spaced from adjacent distal ports, thus staggering the ports circumferentially and/or longitudinally at distal end 201. Although the example of FIG. 5 depicts five separate lumens, it should be understood this is just an example. In embodiments where sheath adapter 200 includes multiple lumens, sheath adapter 200 may have any reasonable number of lumens, for example between about two lumens to about ten lumens.

Figure 6A:
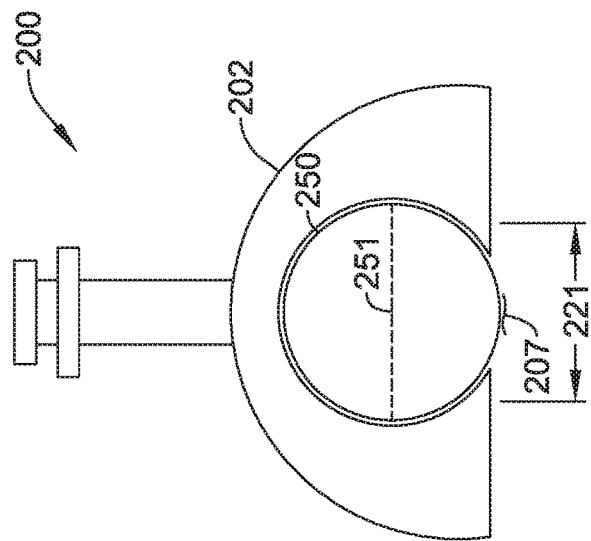
FIGS. 6A-6C are end views of the exemplary sheath adapter of FIGS. 3A-3B along with a shaft of a medical device.

FIG. 6A depicts an end view of proximal end 201 of sheath adapter 200 including channel 205. Channel 205, in different embodiments, may have an inner diameter 223 that ranges from about 5.0 mm to about 9.0 mm, about 6.0 mm to about 9.0 mm, or about 6.5 mm to about 9.0 mm, for example. The inner diameter 223 may be sized to accommodate the shaft of an operative endoscope having an outer diameter ranging from about 5.0 mm to about 9.0 mm, for example. In other embodiments, the inner diameter 223 may range from about 2.0 mm to about 5.0 mm, or about 2.0 mm to about 4.0 mm, for example, such that the inner diameter 223 may be sized to accommodate the shaft of a diagnostic endoscope having an outer diameter ranging from about 2.0 mm to about 5.0 mm, for example. However, in other embodiments, inner diameter 223 may range from about 2.0 mm to about 15.0 mm. In more specific embodiments, diameter 223 may be about 2.0 mm, 3.0 mm, 4.0 mm, 4.5 mm, 5.0 mm, 5.5 mm, 6.0 mm, 6.5 mm, 7.0 mm, 7.5 mm, 8.0 mm, 9.0 mm, 10.0 mm, other any other suitable size. As shown, channel 205 may be formed by an exterior wall of elongate shaft 202 and may be shaped similar to a C or an incomplete circle. Gap 207 may be formed by exterior wall portions 210a, 210b of elongate shaft 202 extending along the length of shaft 202. In general, gap 207 may have a gap width 221, and gap width 221 may have a value that is less than inner diameter 223. For example, gap width 221 may be anywhere between about 60% to about 85% of the value of inner diameter 223. In more specific examples, gap width 221 may be about 60%, 70%, 75%, 80%, or any other suitable percent, of the value of diameter 223.

As mentioned, due to the relative difference between the value of inner diameter 223 and the value of gap width 221, sheath adapter 200 may be securely connected to a shaft of a device, such as an endoscope. For instance, sheath adapter 200 may be configured to snap onto the shaft by passing the shaft of the endoscope laterally (e.g., transverse to longitudinal axis of channel 205) through gap 207 into channel 205. Some example devices that sheath adapter 200 may be configured to connect to include endoscopes, hysteroscopes, resectoscopes, or the like, a shaft of which is represented by shaft 250 in FIGS. 6A-6C.

Figure 6B:
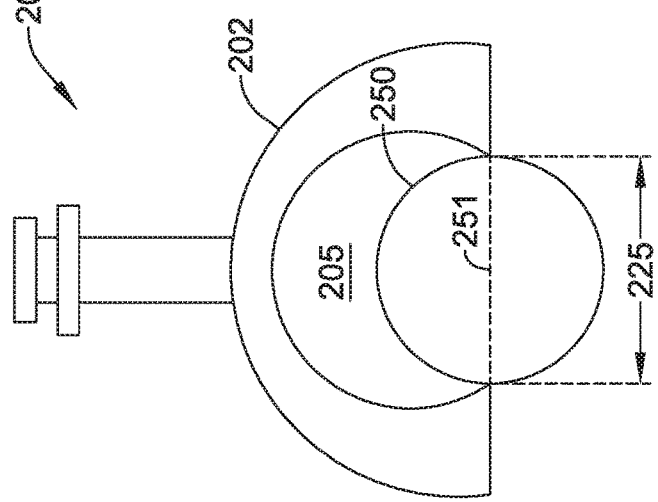
Figure 6C:
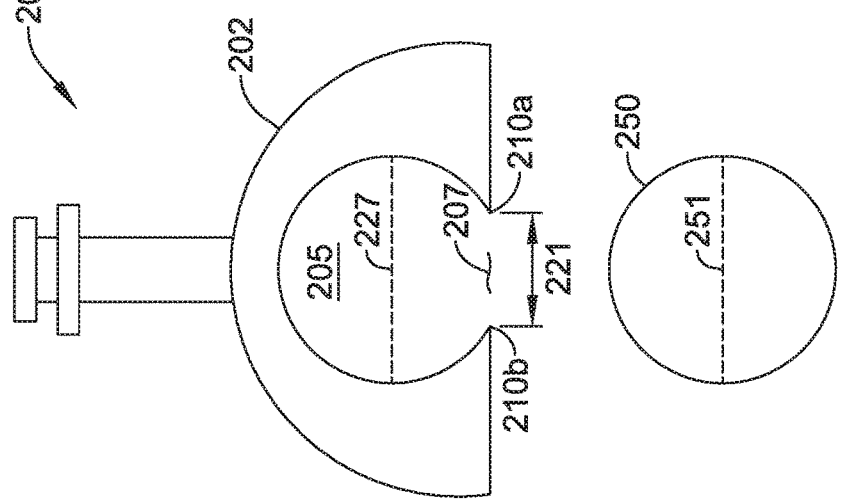

In general, FIGS. 6A-6C depict one example method of connecting sheath adapter 200 to a shaft. Shaft 250 is shown with outer diameter 251, while channel 205 of elongate shaft 202 is depicted with inner diameter 223. In this example, outer diameter 251 may be the same as, or less than, inner diameter 223, but greater than gap distance 221. Accordingly, shaft 250 will not fit through gap 207 to be inserted into channel 205 without flexing edges 210a, 210b apart to increase width of gap 207. In some embodiments, elongate shaft 202 may be made from a material that flexes under sufficient force to widen gap 207.

In such embodiments, when shaft 250 is pressed laterally into gap 207, at a certain level of force, elongate shaft 202 may bend or flex such that gap 207 widens, as depicted in FIG. 6B. For example, gap 207 may widen to have a gap distance 225 at least as large as outer diameter 251 of shaft 250. At this point, shaft 250 may laterally fit through gap 207 and be received within channel 205. The material of elongate shaft 202 may also be a resilient material such that, when shaft 250 is received within channel 205 and the forces on elongate shaft 202 are removed, elongate shaft 202 may return to or toward its original configuration, as shown in FIG. 6C. In these embodiments, gap 207 may return to having gap width 221 less than the outer diameter 251 of shaft 250, which may securely couple sheath adapter 200 to shaft 250, as diameter 251 of shaft 250 is larger than gap distance 221.

Figure 7:
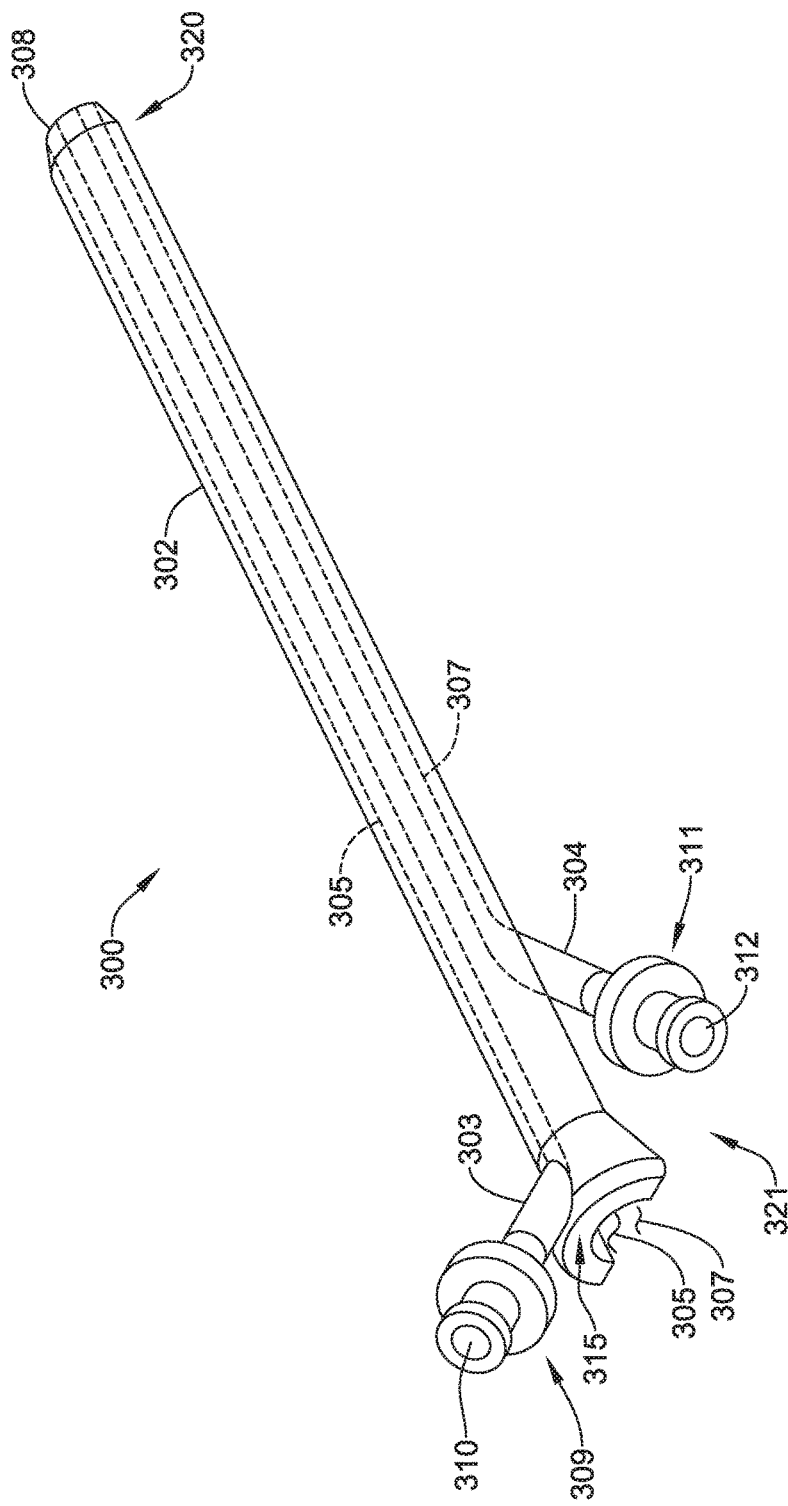
FIG. 7 is perspective view of another exemplary sheath adapter that may be used in conjunction with the hysteroscope of FIG. 1.

FIG. 7 depicts another example embodiment of a sheath adapter similar to sheath adapter 200, sheath adapter 300. Sheath adapter 300 may comprise elongate shaft 302 extending from distal end 320 to proximal end 321, along with extensions 303 and 304, and J-connection 315. In some ways, sheath adapter 300 may be similar to sheath adapter 200 as depicted in FIGS. 3A-3B. For instance, elongate shaft 302 may generally be C-shaped and may define a channel 305, extending the entire length of elongate shaft 302, or along at least a portion of elongate shaft 302. The C-shaped nature of elongate shaft 302 may include gap 307 formed by portions of the wall of elongate shaft 302. Gap 307 may extend longitudinally along the length of sheath adapter 300, permitting lateral access to channel 305 from an exterior of sheath adapter 300.

Further, sheath adapter 300 may include multiple lumens 325, 327 extending along at least a portion of elongate shaft 302. Lumens 325 and 327 may have ports disposed on distal face 308 of elongate shaft 302, or on the sidewall of shaft 302 proximate distal end of elongate shaft 302. Lumens 325 and 327 may additionally be fluidly connected to ports 310 and 312, respectively, disposed proximate proximal end 321 on extensions 303 and 304. It should be understood that although sheath adapter 300 is depicted and described as having only two proximal ports 310, 312, which are disposed on extensions 303, 304, this is an example only. In other embodiments, sheath adapter 300 may have additional or fewer proximal ports and/or additional or fewer extensions. For instance, in some embodiments, each lumen may have its own distal port and its own proximal port, as in FIG. 7. However, in other embodiments, lumens 325, 327 may each have a distal port, but may merge into a single proximal port, for instance where sheath adapter 300 has only a single extension. Even further, although FIG. 7 only depicts two lumens 325, 327, other embodiments may have additional lumens, and each lumen may have a proximal port disposed on separate extensions.

Each of extensions 303, 304 may include connecting portions 309, 311. Connecting portions 309, 311 may be similar to connecting portion 209. For instance, connecting portions 309, 311 may comprise luer fittings or other fittings for sealingly connecting fluid lines or devices to ports 310, 312.

Figure 8:
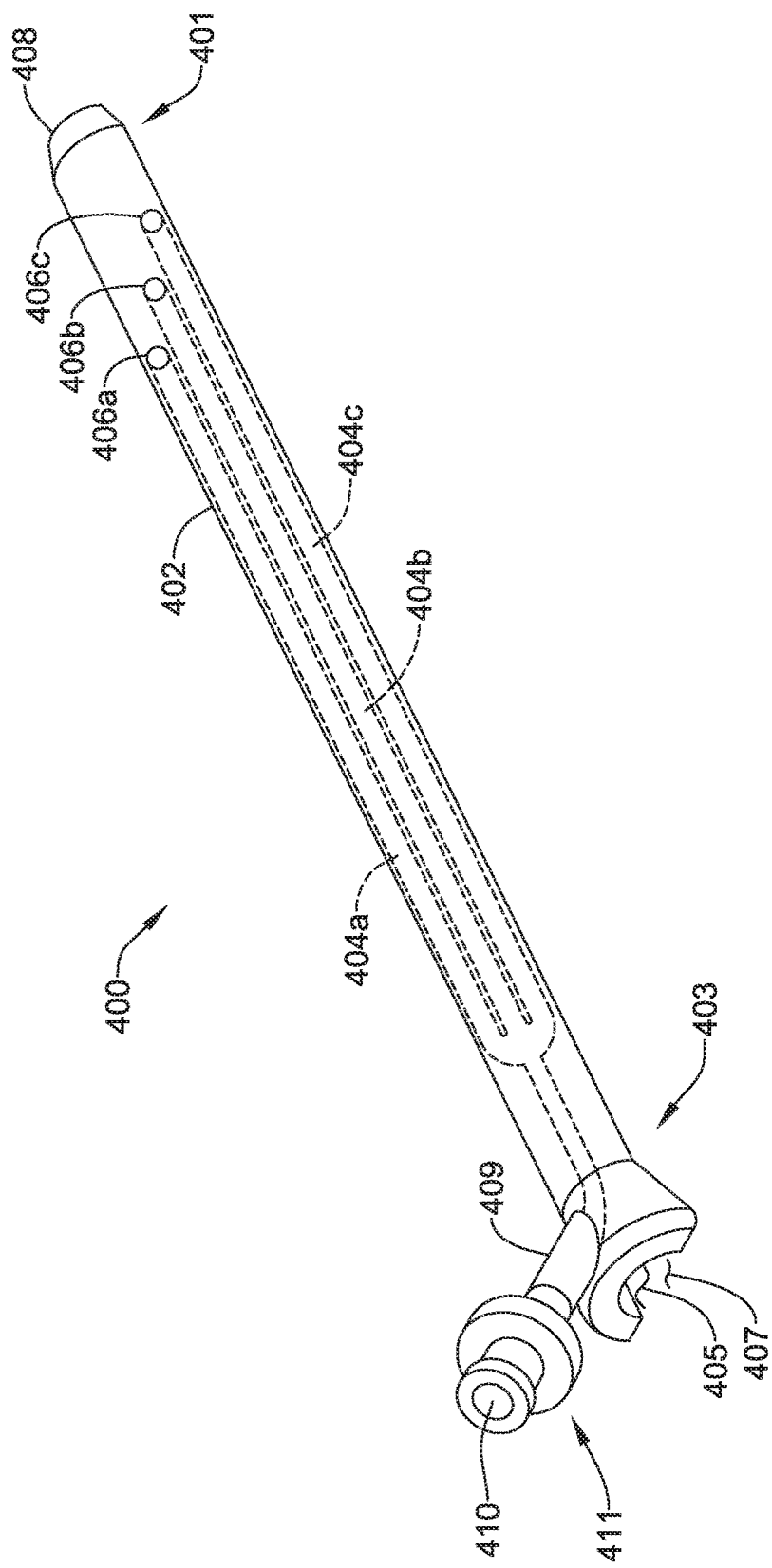
FIG. 8 is perspective view of another exemplary sheath adapter that may be used in conjunction with the hysteroscope of FIG. 1.

FIG. 8 depicts yet another example sheath adapter, sheath adapter 400, which may be similar to sheath adapter 200 or sheath adapter 300. Sheath adapter 400 may comprise elongate shaft 402 extending from distal end 401 to proximal end 403. Similar to sheath adapter 200 and 300, elongate shaft 402 may form a C-shape or have an incomplete circular cross-section, as elongate shaft 402 defines channel 405 opening laterally to an exterior of shaft 402 between edges of shaft 402. Sheath adapter 400 may also include extension 409 with port 410 disposed thereon. In some embodiments, extension 409 may further include connecting portion 411, which may be similar to connecting portions described with respect to other figures.

However, unlike sheath adapters 200 and 300, sheath adapter 400 have ports for one or more lumens disposed on a side of elongate shaft 402. For example, elongate shaft 402 may have one or more lumens 404a-404c extending through at least a portion of elongate shaft 402. Lumens 404a-404c may have distal ports 406a-406c disposed proximate distal end 401 of sheath adapter 400 and may be disposed on a side of elongate shaft 402. However, in other embodiments, at least some of distal ports 406a-406c may be disposed on distal face 408. Further, although FIG. 8 only depicts sheath adapter 400 with three lumens, in other embodiments, sheath adapter 400 may include any reasonable number of lumens. For instance, sheath adapter 400 may include between about two lumens to about ten lumens.

In the embodiment of FIG. 8, lumens 404a-404c may merge at some point within sheath adapter 400, such was within elongate shaft 402, and connect with port 410 disposed proximate proximal end 403. In other embodiments, however, one or more of lumens 404a-404c may have a separate port disposed proximate proximal end 403. Where sheath adapter 400 has multiple lumens merging into a single lumen, as in FIG. 8, when sheath adapter 400 is connected to a pressure sensor (for instance, via connecting portion 11) to turn lumens 404a-404c into static pressure channels, the pressure sensor may still function normally if one of lumens 404a-404c becomes plugged or occluded as the other open lumens will still translate the pressure from distal end 401 to the pressure sensor.

As depicted in FIG. 8, ports 406a-406c may be disposed at varying longitudinal distances from distal face 408, and/or circumferential positions. For example, ports 406a-406c may form a spiraling pattern around elongate shaft 402. In other embodiments, however, ports 406a-406c may form other patterns, such as a ring or series of rings, around elongate shaft 402. In general, ports 406a-406c may be disposed at any desired location proximate distal end 401 and form any desired pattern.

Accordingly, sheath adapters 200, 300, and 400 may provide multiple additional usable lumens or channels when connected to an endoscope, hysteroscope, resectoscope, or the like. For instance, at least one lumen of a sheath adapter may be connected to a pressure sensor, and thus provide a static pressure line for measuring the intra-cavity pressure during a medical procedure. In other instances, at least one lumen of a sheath adapter may be connected to a fluid line and used for fluid inflow or outflow. This may free up a lumen of the scope to be used for other purposes, such as a static pressure channel. In other embodiments, at least one lumen of the sheath adapter may be used for fluid inflow while a pressure sensor may be connected to another lumen of the sheath adapter, turning that lumen into a static pressure channel. This configuration would free up multiple lumens or channels in the scope for other purposes. In still other embodiments, at least one lumen of the sheath adapter may be configured to receive one or more devices. In general, the additional lumens or channels provided by the sheath adapters described herein, when attached to a scope, may be used in conjunction with the lumens or channels of the scope to perform any desired function that is normally performed by one of the lumens or channels situated within the scope.

Additionally, sheath adapters 200, 300, and 400 have all been described as having different features. However, it should be understood that other sheath adapters contemplated by this disclosure may include combinations of features of any of sheath adapters 200, 300, and 400. For example other contemplated sheath adapters may include multiple extensions, as with sheath adapter 300, and lumens that have ports disposed proximate a distal end of the sheath with ports disposed on a side of the elongate shaft of the sheath adapter, as in sheath adapter 400. In general, other sheath adapters may include any combination of features described with respect to sheath adapters 200, 300, and 400.

Figure 9:
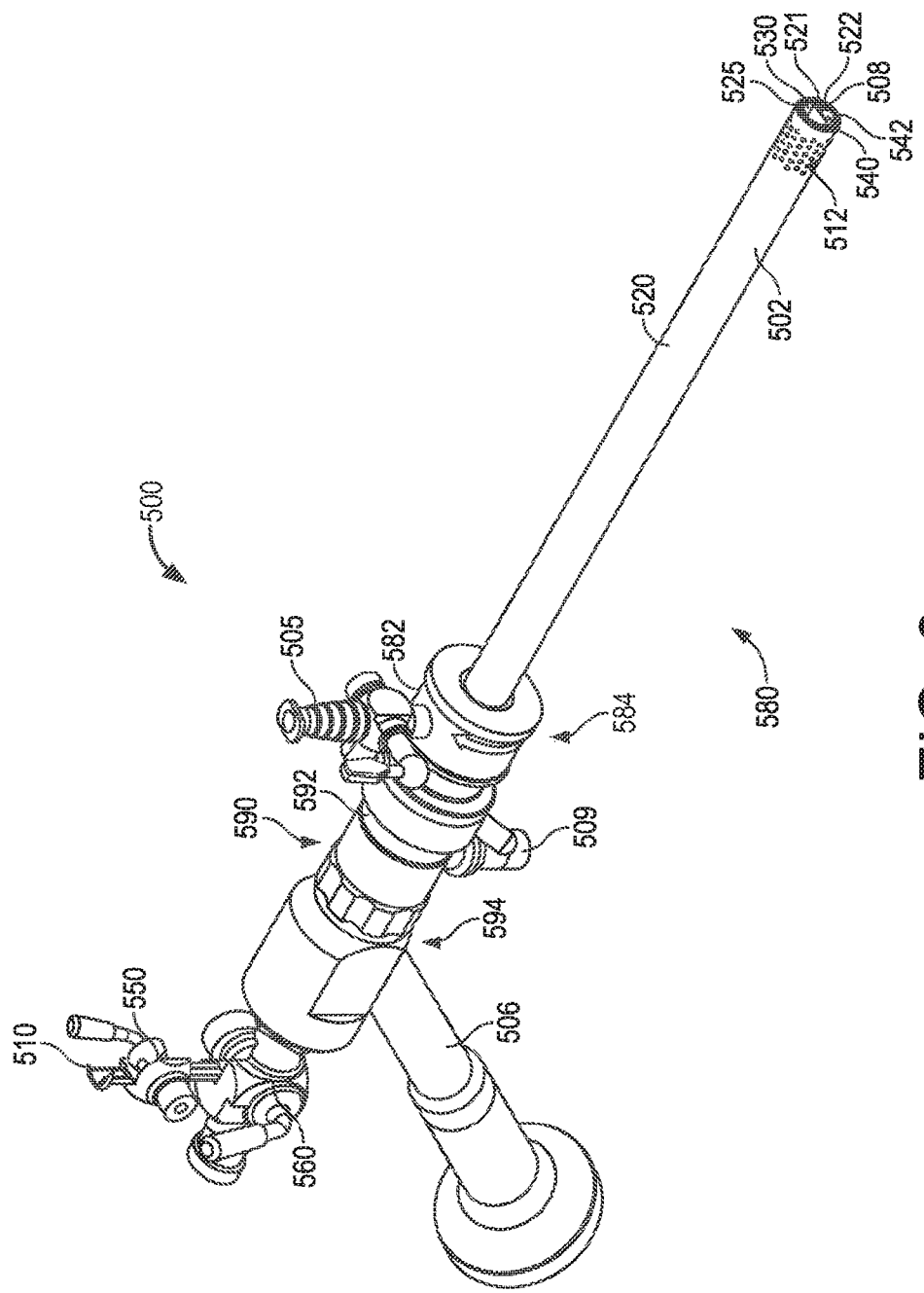
FIG. 9 is a perspective view of an exemplary hysteroscope that may be used in conjunction with any of the sheath adapters disclosed herein.
Figure 10:
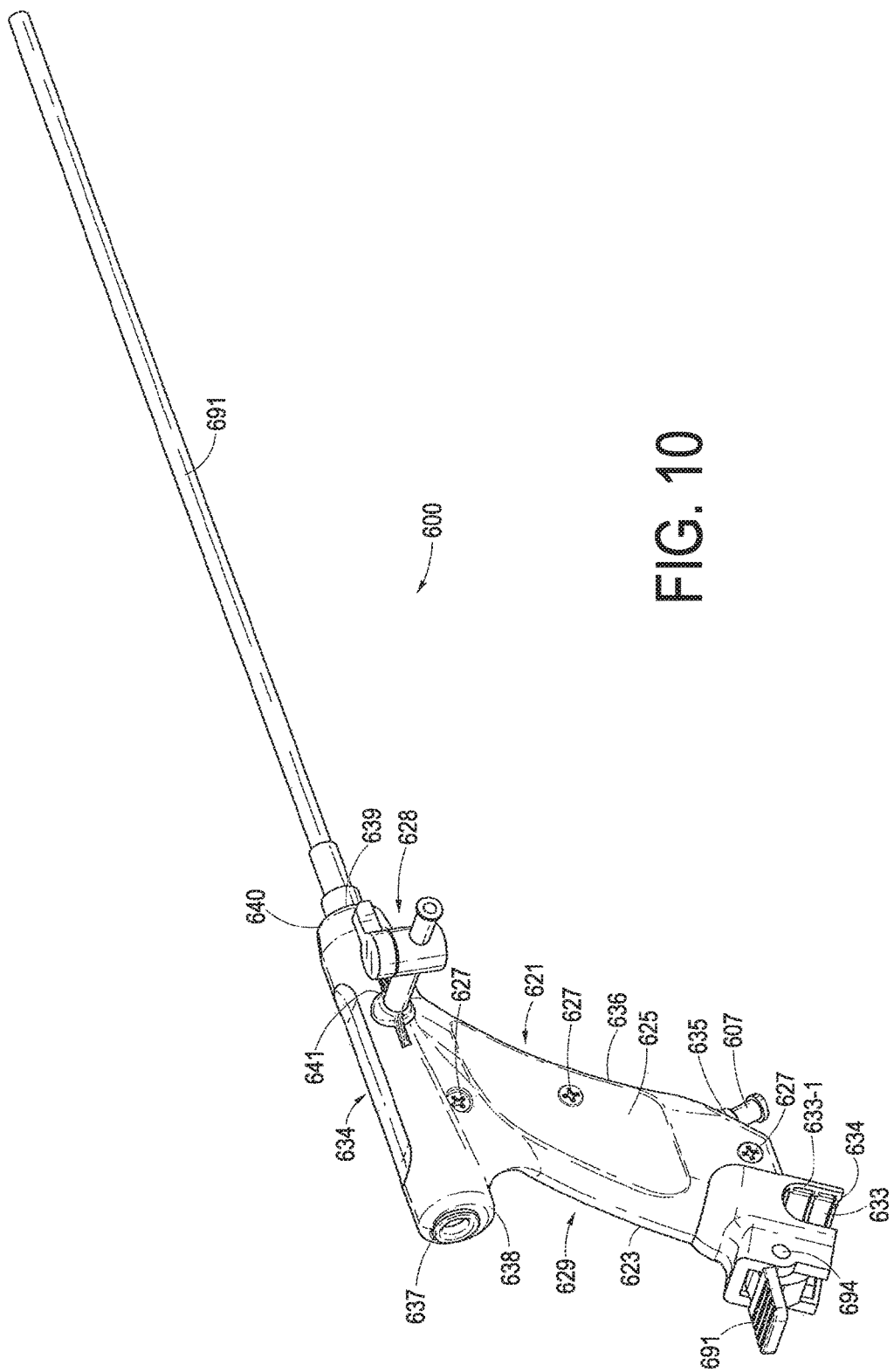
FIG. 10 is a perspective view of an exemplary introducer that may be used in conjunction with any of the sheath adapters disclosed herein.
Figure 11:
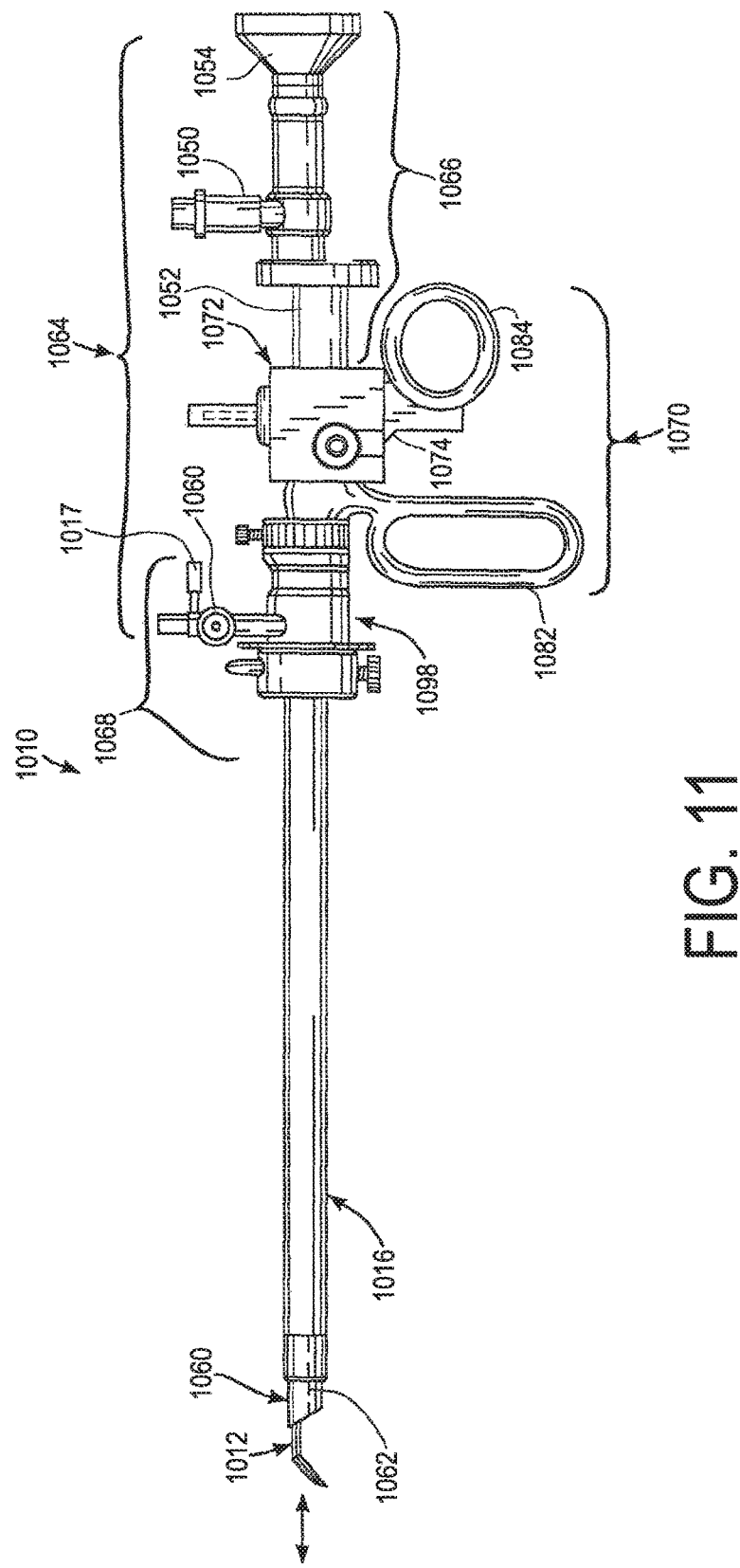
FIG. 11 is a plan view of an exemplary resectoscope that may be used in conjunction with any of the sheath adapters disclosed herein.

In some specific examples, sheath adapters 200, 300, and/or 400 may be configured to cooperate with the specific devices of FIGS. 9-11. For instance, FIGS. 9-11I depict different devices that sheath adapters 200, 300, and/or 400 may cooperate with to provide one or more additional lumens or channels.

Referring to FIG. 9, hysteroscope 500 includes a sheath 580 that has a tube 520 with an inner wall 522 defining a channel 521 therethrough. Distal end 502 of tube 520 includes a plurality of holes 512 in communication with channel 521 for allowing fluid to flow out of an organ through channel 521. Sheath 580 has a proximal portion 584 that includes outflow port 505. Outflow port 505 is in fluid communication with channel 521. Positioned between outflow port 505 and channel 521 is an on/off valve 523 for turning on and off fluid flow from channel 521 to outflow port 505.

Hysteroscope 500 also includes a scope housing 590 that has an elongated member removably receivable in tube 520. The elongated member has an outer wall and an inner wall, and the inner wall defines an inflow channel 530. A proximal portion 594 of scope housing 590 includes inflow port 510, a primary valve 550, and a secondary valve 560, which are fluidly connected to inflow channel 530, for instance through proximal end 507. The elongated member also defines a lens channel 540 that houses an optical lens 542. Scope housing 590 has a proximal portion 594 that includes camera port 506 and light port 509, which are coupled to optical lens 542 by fiber optic lines (not shown). Light travels from light port 509 to distal end 502 of hysteroscope 500 to illuminate objects near distal end 502. Images of those objects are received by optical lens 542, and travel through camera port 506 to a camera to allow the user to view the organ through hysteroscope 500. Lens channel 540 is positioned adjacent to inflow channel 530 to help keep optical lens 542 clear of debris during use. Proximal portion 594 of scope housing 590 also includes a pin 592 receivable in a J-shaped slot (not shown) in sheath 580 to releasably lock scope housing 590 to sheath 580 when member 524 is received in tube 520.

In view of FIG. 9, it can be seen that sheath adapters 200, 300, and/or 400 may be connected to tube 520 to provide one or more additional usable lumens or channels. For example, a pressure sensor may be connected onto a proximal port of the attached sheath adapter to create one or more a static pressure channels in the sheath adapter. Feedback from the pressure sensor may allow a fluid management system to adjust flow rates of fluid through inflow and outflow channels 530 and 521. In other examples, one or more lumens or channels of the sheath adapter may be connected to a fluid outflow or inflow line, and a pressure sensor may be connected directly to sleeve 520 or housing 590, for instance to one of ports 505 or 510, turning the corresponding inflow or outflow channel into a static pressure channel and routing the inflow or outflow channel through the sheath adapter. It should be appreciated that even more combinations of inflow/outflow channels, static pressure channels, and/or working or device channels are possible.

FIG. 10 depicts another example device that may be used with sheath adapters 200, 300, and/or 400. FIG. 10 depicts introducer 600 may comprising a housing 621. Housing 621, in turn, may comprise a left handle half 623 and a right handle half 625. Left handle half 623 and right handle half 625, which may be molded or otherwise fabricated from a rigid polymer or other suitable material, may be joined by a plurality of screws 627. Instead of being joined by screws 627, left handle half 623 and right handle half 625 may be joined using a suitable adhesive, crush pins, or may be welded together ultrasonically or otherwise. Left handle half 623 and right handle half 625 jointly define a hollow, gun-shaped structure comprising a handle portion 629 and a barrel portion 631. Handle portion 629 may be shaped to include an opening 633 provided at its bottom end 634 and an opening 635 provided along its distal face 636 near bottom end 634. A slot 633-1 may be provided in right handle half 625, slot 633-1 extending from opening 633 towards barrel portion 631 for a short distance. Barrel portion 631 may be shaped to include an opening 637 provided at its proximal end 638 and an opening 639 provided at its distal end 640. In addition, barrel portion 631 may be shaped to include a transverse opening 641 provided in right handle half 625 at a location intermediate to proximal end 638 and distal end 640.

The interior surfaces of left handle half 623 and right handle half 625 may shaped to include complementary sets of ribs (not shown). Such ribs may provide structural reinforcement to left handle half 623 and right handle half 625 and may help to maintain the correct positioning and alignment of the components positioned within housing 621.

Introducer 600 may further comprise a manifold (not shown) taking the form of a unitary, branched structure shaped to include a main tubular member and a side tubular member. The main member and the side tubular member may both define lumens which are in fluid communication with each other. The manifold may be coupled to housing 521 with one end positioned in barrel portion 531, where a side wall of the manifold fits tightly within opening 639, and with where an opposite end of the manifold extending distally a short distance beyond distal end 640.

Introducer 600 may further comprise a sheath 691. Sheath 691, which may be extruded or otherwise fabricated from a suitable polymer, may be a rigid, unitary structure shaped to include a proximal end, a distal end, and a side wall. Sheath 691 may be further shaped to include a plurality of longitudinal lumens of fixed shape and size, such lumens including a top lumen, a bottom lumen, and a pair of side lumens. The top lumen may be used as an instrument lumen, the bottom lumen may be used as a visualization lumen, and the side lumens may be used as inflow fluid supply lumens. Openings (not shown) may be provided in side wall of sheath 961 proximate its distal end, such side openings fluidly communicating with the side lumens, for example, to dispense some of the inflow fluid supply conducted distally through the side lumens.

Sheath 691, which is preferably the only component of introducer 600 that is to be inserted into a patient, may be dimensioned to have an outer diameter of about 5.5 mm, with the top lumen having a diameter of about 3 mm, the bottom lumen having a diameter of about 2 mm, and the side lumens each having a diameter of about 1.33 mm. However, it should be understood that the above dimensions for sheath 691 are merely exemplary and may be varied depending upon how introducer 600 is to be used.

Introducer 600 may further comprise an instrument guide assembly mounted within housing 621 for providing a continuous channel aligned with the top lumen of sheath 691 into which a tissue removal device may be inserted. The instrument guide assembly may comprise a guide body. The body, which may be molded or otherwise fabricated from a rigid polymer or other suitable material, may be a unitary tubular structure. The interior surface of the body may taper inwardly from a proximal portion to an intermediate portion to facilitate insertion of the tissue removal device into the intermediate portion and to delimit the extent to which the device may be inserted into the body.

The guide body may be tightly fitted within opening 637 of housing 621 and fixedly secured thereto using a suitable adhesive or the like, with the distal portion of the guide body and the intermediate portion of the body being positioned within barrel portion 631 of housing 621 and with the proximal portion of the body extending through opening 637 and continuing proximally for a short distance beyond proximal end 638 of housing 621.

Valve 628 may be an actively-controlled valve, such as a stopcock valve, or a passively-controlled valve, such as a spring-activated ball valve. Valve 628 may be connected at its output end to a length of tubing (not shown), as well as to a fluid receptacle (not shown), for conducting, as well as collecting, for example, outflow fluid passing through valve 628.

Introducer 600 may further comprise a mechanism for reversibly coupling an endoscope or hysteroscope. This mechanism may comprise a cam lock 691. Lock 691, which may be fabricated from a rigid polymer or other suitable material, may be a unitary structure shaped to comprise a lever and a fulcrum. The fulcrum may be pivotally mounted on housing 621 using a pivot pin 694 inserted through a transverse opening in the fulcrum.

Introducer 600 may further comprise a tube. The tube, which may be fabricated from a suitable polymer or other material, may be a flexible unitary structure shaped to include a proximal end and a distal end. The proximal end may be secured to the distal end of a luer fitting 607 securely mounted within opening 635 of housing 621. The distal end may be positioned within a lumen of the manifold and may be secured in place using an adhesive or other suitable means. Luer fitting 607 may be connected to an output of a fluid supply. In this manner, fluid dispensed through fitting 607 may be conducted to the manifold. Thereafter, the fluid in the manifold may flow distally through the side lumens of sheath 691.

As can be seen, sheath adapters 200, 300, and/or 400 may be used in conjunction with introducer 600 in order to provide one or more additional usable lumens or channels. For example, a pressure sensor may be connected onto a proximal port of the attached sheath adapter to create one or more a static pressure channels in the sheath adapter. Feedback from the pressure sensor may allow a fluid management system to adjust flow rates of fluid through inflow through the side channels. In other examples, one or more lumens or channels of the sheath adapter may be connected to a fluid outflow or inflow line, and a pressure sensor may be connected directly to introducer 600, for instance to luer-fitting 607 or to a port of a connected endoscope or hysteroscope, turning the corresponding channel into a static pressure channel. It should be appreciated that even more combinations of inflow/outflow channels, static pressure channels, and/or working or device channels are possible.

Referring to FIG. 11 resectoscope 1010 represents a conventional or specialized resectoscope that is adapted for use with resecting loop assembly 1012 and return electrode oversheath 1016, according to the present disclosure. Resectoscope 1010 generally includes a proximal handle 1064, and an introducing sheath 1060 having a hollow, tubular shaft 1062 for axially receiving loop assembly 1012. Sheath 1060 also includes a proximal hub 1098 for connecting sheath 1060 to handle 1064 and return electrode oversheath 1016. As shown in FIG. 2, handle 1064 includes a viewing assembly 1066, an irrigant/suction assembly 1068 and an actuation assembly 1070 for axially reciprocating loop assembly 1012 relative to shaft 1062. Actuation assembly 1070 includes a coupling housing 1072 having an outer knob or screw 74 that can be tightened to secure a loop assembly 1012 to an electrically con ducting inner sleeve member of coupling housing 1072. Coupling housing 1072 is axially translatable relative to introducing sheath 1060 so that resecting loop assembly 1012 can be axially translated relative to a distal end of tubular shaft 1062. As shown in FIG. 2, resectoscope 1010 will usually include a finger loop 82 and a thumb loop 1084 suitably connected to housing 1072 for reciprocating housing 1072 and loop assembly 1012 relative to the distal end of shaft 1062. Of course, it will be recognized that other control means for axially reciprocating loop assembly 1012 can be utilized with the present disclosure, such as rotatable knobs, trigger buttons, and the like. As mentioned above, handle 1064 of resectoscope 1010 will also usually include a viewing assembly 1066 and an irrigant/suction assembly 1068. As shown in FIG. 2, viewing assembly 1066 includes a hub 1050, a telescopic lumen 1052 extending through shaft 1062 of introducing sheath 1060 and an eyepiece 1054 coupled to lumen 1052 to permit viewing of the target site by the physician. Alternatively, a camera (not shown) may be attached to the proximal end of hub 1050 to allow display of the surgical site on a video monitor. A fiberoptic light source (not shown) is typically attached to hub 1050 to illuminate the target site. Irrigant/suction assembly 1068 includes proximal hub 1098 of introducing sheath 1060, and a connector 1065 extending from hub 1098 and coupled to a supply line for introducing a sterile irrigant, typically isotonic saline, to the surgical site. Irrigant/suction assembly 1068 may further include valve 1017, which may control fluid flow through connector 1065. Connector 1065 is fluidly coupled to an axial lumen within shaft 1062. Fluid may also be withdrawn through the axial lumen or a second lumen (not shown) within shaft 1062 to withdraw unwanted or excess fluids from the surgical site and to facilitate the surgeon's view.

As can be seen, sheath adapters 200, 300, and/or 400 may be used in conjunction with introducer resectoscope 1010 in order to provide one or more additional usable lumens or channels. For example, a pressure sensor may be connected onto a proximal port of the attached sheath adapter to create one or more a static pressure channels in the sheath adapter. Feedback from the pressure sensor may allow a fluid management system to adjust flow rates of fluid through inflow through irrigant/suction assembly 1068. In other examples, one or more lumens or channels of the sheath adapter may be connected to a fluid outflow or inflow line, and a pressure sensor may be connected directly to resectoscope 1010, for instance to connector 1065, turning channel connected to connector 1065 into a static pressure channel. It should be appreciated that even more combinations of inflow/outflow channels, static pressure channels, and/or working or device channels are possible.

Those skilled in the art will recognize that the present disclosure may be manifested in a variety of forms other than the specific embodiments described and contemplated herein. Specifically, the various features described with respect to the various embodiments and figures should not be construed to be applicable to only those embodiments and/or figures. Rather, each described feature may be combined with any other feature in various contemplated embodiments, either with or without any of the other features described in conjunction with those features. Accordingly, departure in form and detail may be made without departing from the scope of the present disclosure as described in the appended claims.

What is claimed is:

1. A sheath for use with a medical device, the sheath comprising:
    a C-shaped elongate shaft having a circularly shaped cross-section with a gap having a gap width, the gap extending along an entire length of the sheath from a proximalmost extent of the sheath to a distalmost extent of the sheath, the C-shaped elongate shaft configured to fit onto a shaft of the medical device;
    a first lumen extending at least partially along a length of the C-shaped elongate shaft, the first lumen having a first port disposed proximate the distal end of the C-shaped elongate shaft and a second port disposed proximate the proximal end of the C-shaped elongate shaft;
    a second lumen extending at least partially along the length of the C-shaped elongate shaft, the second lumen having a first port disposed proximate the distal end of the C-shaped elongate shaft and a second port disposed proximate the proximal end of the C-shaped elongate shaft;
    wherein the second port of the second lumen is the second port of the first lumen;
    a connecting member disposed at the second port; and
    a pressure sensor connected to the connecting member to seal off the first and second lumens thereby forming static fluid columns within the first and second lumens in fluid communication with the pressure sensor.

2. The sheath of claim 1, wherein the first port of the first lumen is disposed on a distal-facing surface of the C-shaped elongate shaft.

3. The sheath of claim 1, wherein the first port of the first lumen is disposed on a side of the C-shaped elongate shaft.

4. The sheath of claim 1, wherein the C-shaped elongate shaft is configured to securely snap onto the shaft of the medical device.

5. The sheath of claim 1, wherein the circularly shaped cross-section defines a channel having a channel diameter, and wherein the gap width is less than the channel diameter.

6. The sheath of claim 1, wherein the C-shaped elongate shaft is configured to flex in order to fit onto the shaft of the medical device by passing the shaft laterally through the gap.

7. The sheath of claim 1, wherein the medical device comprises an endoscope.

8. The sheath of claim 1, wherein the first port of the second lumen is disposed on a distal-facing surface of the C-shaped elongate shaft.

9. The sheath of claim 1, wherein the first port of the second lumen is disposed on a side of the C-shaped elongate shaft.

10. A medical device sheath comprising:
    an elongate shaft having a length extending from a proximal end to a distal end, a wall of the elongate shaft defining a channel with a longitudinally extending opening extending through the wall such that the elongate shaft only partially surrounds the channel, the longitudinally extending opening extending from a proximalmost extent of the sheath to a distalmost extent of the sheath, the channel configured to receive a shaft of a medical device laterally therein;
    a first lumen extending at least partially along the length of the elongate shaft within the wall of the elongate shaft, a second lumen extending at least partially along the length of the elongate shaft within the wall of the elongate shaft, and a third lumen extending at least partially along the length of the elongate shaft within the wall of the elongate shaft;

wherein the first lumen, the second lumen, and the third lumen merge at some point within the elongate shaft and connect with a proximal port disposed proximate the proximal end of the elongate shaft;

wherein the first lumen includes a first distal port disposed proximate the distal end of the elongate shaft, the second lumen includes a second distal port disposed proximate the distal end of the elongate shaft, and the third lumen includes a third distal port disposed proximate the distal end of the elongate shaft;

wherein the first distal port, the second distal port, and the third distal port form a spiraling pattern around the elongate shaft;

wherein the medical device is laterally received into the channel through the longitudinally extending opening in the wall of the elongate shaft; and a pressure sensor connected to the proximal port to seal off the first, second, and third lumens thereby forming static fluid columns within the first, second, and third lumens in fluid communication with the pressure sensor.

11. The medical device sheath of claim 10, further comprising a connection member disposed at the proximal end of the elongate shaft, the connection member configured to connect to the medical device.

12. The medical device sheath of claim 10, wherein the medical device is an endoscope or a hysteroscope.

13. The medical device sheath of claim 10, wherein the channel has a channel diameter, and wherein the channel diameter is less than or equal to a diameter of the shaft of the medical device.

14. The medical device sheath of claim 10,
wherein a width of the opening is smaller than a diameter of the shaft of the medical device, and
wherein the wall of the elongate shaft is configured to flex to receive the shaft of the medical device through the longitudinally extending opening of the channel within the channel.

* * * * *